United States Patent [19]

Nomura et al.

[11] Patent Number: 5,055,554

[45] Date of Patent: Oct. 8, 1991

[54] RENAL GROWTH PROMOTER AND PROCESS FOR THE PRODUCTION OF THE SAME

[75] Inventors: Kaoru Nomura, Musasino; Kazutaka Ohmura, Kashiwa; Yuri Shirakura, Koufu; Yasunori Nakamura, Yokohama; Makoto Ujihara, Tokyo; Satoshi Toyoshima, Chiba; Kazuo Yamamoto, Tokyo; Toshiaki Osawa, Tokyo; Kazuo Shizume, Tokyo, all of Japan

[73] Assignee: The Calpis Food Industry Co., Ltd., Tokyo, Japan

[21] Appl. No.: 299,928

[22] Filed: Dec. 1, 1988

Related U.S. Application Data

[63] Continuation-in-part of Ser. No. 269,150, Oct. 27, 1988, abandoned.

[30] Foreign Application Priority Data

Apr. 20, 1987 [JP] Japan .................................. 62-95277
Dec. 3, 1987 [JP] Japan ................................ 62-304422
Oct. 5, 1988 [JP] Japan ................................ 63-249970

[51] Int. Cl.$^5$ ........................ C07K 7/20; A61K 37/24
[52] U.S. Cl. ................................... 530/313; 520/397; 520/398; 520/399
[58] Field of Search ............... 530/398, 399, 313, 397; 514/8

[56] References Cited

U.S. PATENT DOCUMENTS 4,383,035  5/1983  Sugimoto .

OTHER PUBLICATIONS

Nomura, K. et al., *Proc. Natl. Acad. Sci.*, 79: 6675–6679, Nov. 1982.
Stenesh, *Dictionary of Biochemistry*, p. 168, 1975.
Stedman, *Stedman's Medical Dictionary*, 24th Ed., p. 730, 1982.
Grant, *Hackh's Chemical Dictionary*, 4th Ed., p. 361, 1969.
Nomura et al., *Endocrinology*, 123 (2): 700–711, Aug. 1988.
Nomura et al., *Endocrinology*, 124(2): 712–719, 1989.
Nomura et al., *Nephron*, 39: 255–260, 1985.
Nomura, K. et al., *Endocrinology*, 116(2), p. 616–621, 1985.
Ward, D. et al., *Int. J. Peptide Protein Res.*, 27, pp. 70–78, 1986.
Yano, M. Acta Abst. Gynaec, Jpn. 37(5): pp. 703–712, 1985.
Sairam, M. R. (1980), "Deglycosylation of Ovine Pituitary Lutropin Subunits: Effects on Subunit Interaction and Hormone Activity", *Archives of Biochemistry and Biophysics*, vol. 204, No. 1, Oct., pp. 199–206.
Bahl et al. (1980), "A Novel Carbohydrate Structure in Bovine and Ovine Luteinizing Hormones", *Biochemical and Biophysical Research Communications*, vol. 96, No. 3, Oct. 16, pp. 1192–1199.
Austin III et al., *Nephron*, "Humoral Regulation of Renal Growth", vol. 27, pp. 163–170.
Nomura et al., Chemical Abstracts, vol. 110, No. 13, Mar. 27, 1989, p. 89, Abstract 108335s.

(List continued on next page.)

*Primary Examiner*—Howard E. Schain
*Assistant Examiner*—Susan M. Perkins
*Attorney, Agent, or Firm*—Browdy and Neimark

[57] ABSTRACT

The present invention relates to a renal growth promoter based on the finding that luteinizing hormone or an isoform thereof has an effect of promoting renal growth.

It was prevnisly unknown that luteinizing hormone or an isoform thereof has an effect of promoting renal growth.

With the present invention, it is expected that kidneys suffering from a decreased in the number of renal cells or a lowering in the renal function may be activated by administering luteinizing hormone or an isoform thereof.

11 Claims, 1 Drawing Sheet

OTHER PUBLICATIONS

Matteri, R. L. et al., "Characterization of Equine Luteinizing Hormone by Chromatofusing", *Biology of Reproduction*, 36, 261–269 (1987).

Baldwin, David M. et al., "An In Vitro Study of LH Release, Synthesis and Heterogeneity in Pituitaries from Proestrous and Short-Term Ovariectomized Rats", *Biology of Reproduction* 34, 304–315 (1986).

Johnston, Robyn C. et al., "High-Performance Liquid Chromatography of Amino Acids, Peptides and Proteins; LXXXV. Separation of Isoforms of the Glycoprotein Hormones from Human Pituitary Extracts," *Journal of Chromatography* 397, 389–398 (1987).

Strickland, Thomas W. et al., "Contribution of Subunits to the Function of Luteinizing Hormone/Human Chorionic Gonadotropin Recombinants", *Endocrinology* 109(6), 1933–1942 (1981).

Chemical Abstracts, vol. 102, No. 11, Abstract No. 90348W (Chem. Abstr. 102:90348W), Mar. 18, 1985 (18.03.85), Columbus, Ohio, Nomura et al.

Nippon Rinsho, 44 (1), Separate Issue, 84–88 (Jan. 1, 1986).

M. Yano, *J. Jap. Tocol. Gynecol.*, 37 (5), 703–712 (1985).

RENAL GROWTH PROMOTER AND PROCESS FOR THE PRODUCTION OF THE SAME

This is a continuation-in-part application of parent application, Ser. No. 07/269,150, filed Oct. 27, 1988, now abandoned.

TECHNICAL FIELD

This invention relates to a renal growth promoter and a process for the production of the same.

More particularly, it relates to a renal growth promoter which comprises luteinizing hormone having an activity of promoting renal growth or an isoform thereof as an active ingredient.

The present invention is based on the finding that luteinizing hormone or an isoform thereof has an effect of promoting renal growth. Thus it is expected that the administration of the renal growth promoter of the present invention would increase the number of renal cells or enhance a renalfunction in the kidney suffering from a decrease in renal cells or a lowering in the renal function. The present invention makes a valuable contribution to the medical and pharmacological fields.

BACKGROUND ART

It is previously unknown that luteinizing hormone or an isoform thereof has an effect of promoting renal growth.

The present inventors concentrated their attention on the fact that hypophysectomized mice would show a significant decrease in the renal weight and decided there might be some factor controlling renal growth in the pituitary. Thus they attempted to find a renal growth factor present in the pituitary. Consequently they obtained a fraction containing a hormone-like component promoting renal growth from the pituitary and named the unisolated component promoting renal growth RGF (or renotropin) (cf. Nippon Rinsho, 44 (1), separate issue, 84–88 (Jan. 1986)).

PROBLEMS TO BE SOLVED BY THE INVENTION

Figure 1:
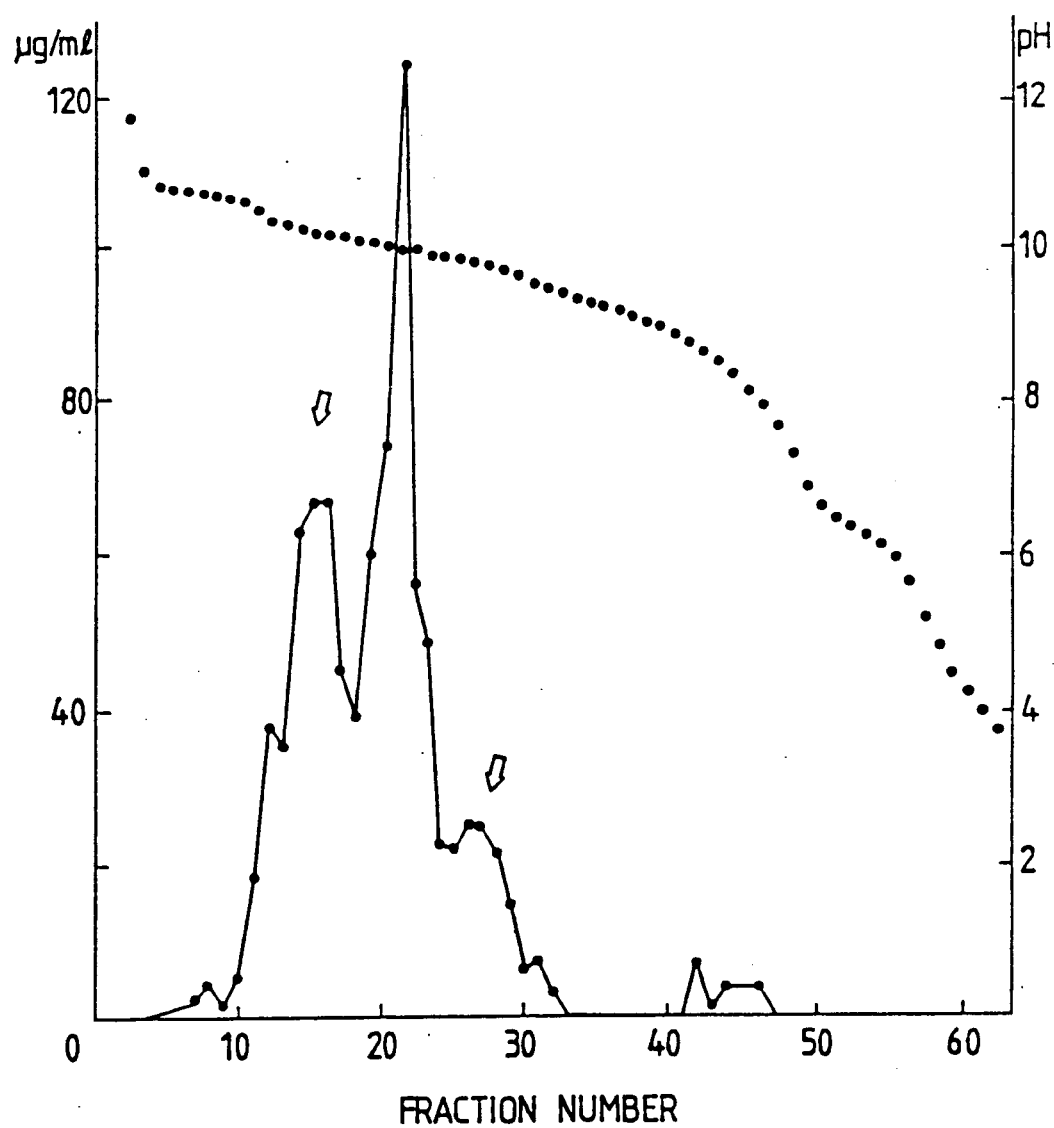
FIG. 1 shows the protein concentration of each fraction obtained by isoelectric focusing of a crude renal growth factor in Example 1.

However it has been found that the RGF-containing fraction thus obtained is a crude product which shows an unstable activity and contains various contaminants having antagonistic effects.

In order to isolate the RGF as a single component, the present inventors conducted further studies. As a result, they unexpectedly found that a single band of an active ingredient could be obtained by fractionating and purifying the crude RGF-containing fraction described above according to the difference in isoelectric points.

The analysis of this single band and the determination of the primary structure thereof surprisingly revealed that it is an isoform of the luteinizing hormone. The fact that the RGF-containing fraction is a mixture of isoforms of luteinizing hormone, was also found.

It is known that luteinizing hormone is not a single compound but glycoproteins comprising a plurality of isoforms. This is caused by the microstructural polymorphism thereof.

It was reported that ovine luteinizing hormone had heterogeneous amino-terminal sequences on the $\alpha$ subunit and heterogeneous carboxyl-terminal sequences on the $\beta$ subunit (D. N. Ward, Int. J. Peptide Protein Res., 27, 70–78 (1986)). It was further reported that the human luteinizing hormone was divided into seven peaks by column electrofocusing (cf. M. Yano, Acta. Abst. Gynaec. Jpn., 37 (5), 703–712 (1985)).

As a matter of course, it had never been previously known that the luteinizing hormone and each isoform thereof would have the effect of promoting renal growth.

Subsequent studies by the present inventors have revealed that the highest activity of promoting renal growth is achieved by an isoform of the luteinizing hormone wherein a subunit $\alpha_3$ is bound to another subunit $\beta_3$.

The present invention first relates to a renal growth promoter comprising a luteinizing hormone or an isomer thereof as an active ingredient. It is preferable that said isoform of luteinizing hormone be comprised of a subunit $\alpha_3$ bound to another subunit $\beta_3$.

The present invention further provides a process for production of the isoform of luteinizing hormone with an activity of promoting renal growth, which comprises fractionating and purifying a crude renal growth factor of luteinizing hormone (mixture of isoforms), according to the difference in isoelectric points.

In accordance with the present invention, the amount of the neutral glyco-chain component among the glyco-chain component in $\beta$ subunit in each isoform of luteinizing hormone as herein isolated was measured, while the renal growth promoting activity thereof was also measured.

The present invention further embodies the isoform containing 30% or more neutral glyco-chain component in the glyco-chain components composition of the $\beta$ subunit of the luteinizing hormone which has an excellent renal growth promoting activity. Of course, it has not previously been known at all that the isoformer possessed a renal growth promoting activity.

The present invention relates to a luteinizing hormone which contains 30% or more neutral glyco-chain component in the glyco-chain component composition of the $\beta$ subunit of luteinizing hormone, and it also relates to a renal growth promoter containing, as an active ingredient, the luteinizing hormone which contains 30% or more neutral glyco-chain component in the glyco-chain component composition of the $\beta$-subunit of luteinizing hormone.

Further, the present invention also embodies the isoform containing 18% or more neutral glyco-chain component in the glyco-chain component composition of the $\beta$ subunit of luteinizing hormone which has an excellent renal growth promoting activity.

The present invention relates to a luteinizing hormone which contains 18% or more neutral glyco-chain component in the glyco-chain component composition of the $\beta$ subunit of luteinizing hormone, and it also relates to a renal growth promoter containing, as an active ingredient, the luteinizing hormone which contains 18% or more neutral glyco-chain component in the glyco-chain component composition of the $\beta$ subunit of luteinizing hormone.

The fractionation and purification treatment according to the difference in isoelectric point as described herein means a treatment whereby ampholytes such as proteins are fractionated from each other according to the inherent isoelectric point of each material and then separately collected. It may be carried out using, for example, chromatofocusing or electrofocusing.

As the crude renal growth factor to be used as the starting material in the present invention, crude luteinizing hormone extracts can be obtained from urine, blood or organs of mammals such as mouse, sheep or swine. Alternatively, a crude product obtained from a culture system which is artificially prepared through genetic engineering may be used. Further a material obtained from a, synthetic chemical reaction system may be employed. A mixture of an isomer of luteinizing hormone having the effect of promoting renal growth with those having no such an effect is employed as the starting material.

For example, the crude renal growth factor is obtained from an organ in the following manner. An aqueous solution of ammonium sulfate is added to the pituitary and the resulting mixture is homogenized and centrifuged. The supernatant is purified and lyophilized. Then the lyophilized material is dissolved and purified by a series of treatments, for example, SP Sephadex chromatography, Sephadex G100 chromatography, CM celluose chromatography, Con. A chromatography and Sephadex G100 chromatography to obtain a crude renal growth factor of luteinizing hormone comprising a mixture of plural isoforms.

The crude renal growth factor thus obtained can be used directly a renal growth promoter, as having the renal growth promoting activity of 112% as shown in Example 1.

The crude renal growth factor obtained may be subjected to fractionation and purification treatment according to the difference in isoelectric points, whereby each isoform having the renal growth promoting activity can be obtained as a single band.

In general, luteinizing hormone is a glycoprotein, which is an associated substance composed of two protein subunits, an $\alpha$ subunit and $\beta$ subunit and it has already is known that the $\alpha$ subunit has glyco-chains bonded to two asparagines and the $\beta$ subunit has a glyco-chain bonded to one asparagine.

Luteinizing hormone is produced in the pituitary gland and is differentiated from other glycoproteins, such as chorionic gonadotropic hormone, in that the glyco-chain terminals in the former are sulfated, and sialated to some degree.

The glyco-chain of luteinizing hormone is known as a typical form of the so-called asparagine-bonded glyco-chain. The saccharide components that constitute the glyco-chain are essentially monosaccharides including mannose, fructose, galactose, glucose, N-acetylglucosamine and N-acetylgalactosamine. All the monosaccharides constituting the said glyco-chain skeletons are neutral. When a sulfuric acid and/or a sialic acid is(are) added to any position of the said glyco-chain skeleton, the resulting glyco-chain is acidified. The number of the acids is generally one or two, but it may be more than two. In the present invention, when one or more sulfuric acids and/or sialic acids is(are) added to the glyco-chain, the resulting glyco-chain is called an acidic glyco-chain, while that having neither the acid group nor the acid is called a neutral glyco-chain.

It is well known that the typical asparagine-bonded glyco-chain as a glyco-chain structure of glycoproteins includes various structural modifications. Making a general classification, mannose-rich type, complex type and hybrid type structures are well known, and further modifications of these have been reported. There may be numerous modifications, for example, due to the presence or absence of fructose or bisect N-acetylglucosamine, presence or absence of N-acetylgalactosamine in place of galactose, or presence of single chain, double chain, triple chain or quadruple chain from mannose as the branching point, as well as presence or absence of sialic acid or sulfuric acid added. Typical examples of the heterogenity can be found in the literature. There are many of the said heterogeneous modifications also in the glyco-chains added to luteinizing hormone.

In accordance with the present invention, the luteinizing hormone containing 30% or more neutral glyco-chain component in the $\beta$ subunit was first fractionated and this has been found to be a luteinizing hormone having an excellent renal cell DNA synthesis promoting activity. It is a new finding.

In accordance with the present invention, the luteinizing hormone containing 18% or more neutral glyco-chain component in the $\beta$ subunit was also newly fractionated and this has also been found to be a luteinizing hormone having an excellent renal cell DNA synthesis promoting activity. It is another new finding.

Accordingly, each substance with a single band obtained by fractionation and purification of the crude renal growth factor using the difference in isoelectric points was analyzed to measure the glyco-chain component content. The fraction having a neutral glyco-chain component in an amount of 30% or more and the fraction having the same in an amount of 18% or more is separated whereby a luteinizing hormone (isomer) having a higher renal growth promoting activity can be obtained.

The material having an activity of promoting renal growth obtained as a single band may be further separated into the constituting subunits $\alpha$ and $\beta$. As a matter of course, the renal growth promoting activity will disappear after dividing the material into these subunits.

The separation may be carried out by, for example, reverse phase liquid chromatography. In the separation pattern, the subunits $\alpha$ and $\beta$ each show a plurality of peaks depending on the length of amino acids' chains. It has been confirmed that these peaks correspond to several shorter amino acids' chains obtained by cutting the subunits $\alpha$ and $\beta$, such chains have been reported previously.

The subunits present within each peak obtained in the course of the reverse phase liquid chromatography disclosed herein (see Example 1) represent a different group of subunits. Thus, the $\alpha$ subunits which elute in the third peak, having the longest amino acid chain length, are considered a single group of subunits herein and are referred to as $\alpha_3$, the $\alpha$ subunits which elute in the second peak are referred to as $\alpha_2$, and the $\alpha$ subunits which elute in the first peak are referred to as $\alpha_1$. The same is true of the $\beta$ subunit peaks.

Although a compound comprising a subunit $\alpha_3$ bound to another subunit $\beta_3$ has a slight luteinizing hormone activity, it is different from other isoforms of luteinizing hormone in that it has a remarkable, renal growth promoting activity.

The subunits $\alpha_3$ and $\beta_3$ undergo the least cuttings. Thus, the term "$\alpha_3$" and the term "$\beta_3$" as used in the present specification and claims is intended to mean the $\alpha$ and $\beta$ subunits, respectively, which are members of the group which have the longest amino acid chain length, i.e., those subunits which elute with the third peak upon reverse phase liquid chromatography under the conditions described herein. Among the various recombinations of subunits which are bound to each other again, the ones having the subunits $\alpha_3$ and $\beta_3$ show the highest activity of promoting renal growth.

Measurement of glyco-chain component content can be carried out by, the following method.

Method of Measurement of Glyco-chain Component Content

For cutting the bond between the asparagine residues in glyco-chain, either the chemical method or the enzymatical method can be employed. However, the former is preferable, as it is free from cutting failure. In the present invention, the hydrazine decomposition method, which is illustrated in Matsushima et al, *Bull. Chem. Soc. Jpn.*, 30, 48, '57 and in Z. Yosizawa et al, *Biochim. Biophys. Acta*, 121, 417, '66, was employed. Using the method of S. Takasaki et al, *Method in Enzymology* (edited by V. Ginsburg, Academic Press, New York, Vol. 83, 263, '82), the reducing terminal of the glyco-chain, as cut out from asparagine residue by a conventional method, is labeled with tritium and then used in the subsequent quantitative analysis.

The tritium-labeled glyco-chain is separated and fractionated by an anion-exchange chromatography such as DEAE Sephacel ® into a neutral glyco-chain fraction and an acid glyco-chain fraction, each of which is quantitatively measured. From these values the percentage of the neutral glyco-chain component content can be obtained.

However, a measurement error of about 10% or so of the value measured may be expected, due to degradation of the reactants during the chemical reaction as well as from the degradation of the products during the column chromatography operation.

EXPERIMENTAL EXAMPLE

A sufficient amount of the lyophilized powder of each fraction of pI 10.32 to 10.15 and pI 10.15 to 9.89 was obtained as described in Example 1 below, to be used as a sample. It was subjected to high performance liquid chromatography to fractionate into subunits $\alpha$ and $\beta$.

Using a reverse phase column, each sample was fractionated with a linear gradient system of water-organic solvent (acetonitrile/isopropanol=3/7) in the presence of 0.1% trifluoroacetic acid, whereby each fraction was collected. The $\alpha$ subunit as eluted out relatively early and $\beta$ subunit eluted out late. Next, each of the fractions was dried to powder under reduced pressure.

About 1 mg of the R subunit powder of each fraction of pI 10.32 to 10.15 and pI 10.15 to 9.89 was weighed in a test tube and 1 ml of anhydrous hydrazine was added thereto. This was heated at 105° C. for 4 hours in the presence of hydrazine sulfate as a catalyst. After the reaction, hydrazine was evaporated out under a reduced pressure. From 0.5 to 1 ml of an aqueous 4.5 M sodium acetate solution was added to the resulting residue, and acetic anhydride was added thereto several times, totaling 100μl, with stirring. After being allowed to stand at room temperature for 30 minutes, it was desalted by treatment in Sephadex G25 ® column to obtain an oligosaccharide fraction. Next, this was concentrated under a reduced pressure to dryness.

Subsequently, 100 μl of water was added to the dry solid and dissolved and an excess amount (2.5 mCi) of $NaB^3H_4$ (in the form of 0.1 M sodium hydroxide solution) was added thereto to reduce the solid for 16 hour at room temperature. After the reaction, 0.5 ml of 1 N acetic acid was added to the reaction mixture, whic was then desalted by treatment in Dowex 50W-X8 col umn. The eluted fraction was concentrated to drynes: Next, in order to remove boric acid from the solic several milliliters of methanol was added thereto an subjected to reduced pressure three times. Then thi was subjected to paper chromatography using a devel oper solvent of ethyl acetate/acetic acid/formic acid/ water (18/3/1/4, v/v) and Whatman 3 MM filter paper whereupon the radioactive site was extracted witl water to recover the glyco-chain.

Next, the sample was dissolved in 2 mM tris-hydro chloric acid buffer (pH 7.4) and then subjected to DEAE-Sephacel ® (Pharmacia) column as equilibratec with the same buffer, whereupon the passed-througl fraction was collected. This was neutral glyco-chair fraction (N). The sodium chloride concentration in the same buffer was elevated up to 100 mM by linear gradi ent, and the fraction as eluted at about 25 mM, 50 mM or 75 mM or so was called acid glyco-chain fractior (A-1), (A-2) or (A-3), respectively.

The strength of the radioactivity of each fraction wa: measured by conventional method where the respective lots were varied.

The value of each of N, A-1, A-2 and A-3 of each sample was shown in Tables 1 and 2 below, a percent age.

TABLE 1

|  | N | A-1 | A-2 | A-3 | Total |
|---|---|---|---|---|---|
| pI 10.32 to 10.15 | 34.1 | 35.5 | 2.1 | 28.3 | 100 |
| pI 10.15 to 9.89 | 15.4 | 38.2 | 5.0 | 41.4 | 100 |

TABLE 2

|  | N | A-1 | A-2 | A-3 | Total |
|---|---|---|---|---|---|
| pI 10.32 to 10.15 | 19.5 | 32.1 | 1.7 | 46.7 | 100 |
| pI 10.15 to 9.89 | 10.0 | 31.9 | 4.9 | 53.2 | 100 |

Now Examples of the present invention will be given.

EXAMPLE 1

10 mM of phenylmethylsulfonyl fluoride was added to approximately 350 g of porcine pituitary and 1 liter of a 0.15 M aqueous solution of ammonium sulfate. The resulting mixture was homogenized in a Waring blender for two minutes while cooling. After adjusting the pH value to 4.0, the homogenized mixture was allowed to stand for a sufficient period of time under cooling. Then it was centrifuged and the supernatant was collected. After further adjusting the pH value to 3.0 with a 0.5 M aqueous solution of metaphosphoric acid, the resulting solution was centrifuged and the supernatant was collected. After adjusting the pH value of the supernatant to 6.5 to 7.0, ammonium sulfate was added thereto until 50% saturation was achieved. Then the mixture was allowed to stand for a sufficient period of time again under cooling. Subsequently it was centrifuged. The precipitate was collected and suspended in 50 to 100 ml of a 0.2 M solution of dibasic potassium phosphate. The suspension was transferred into a dialysis tube and sufficiently dialyzed under cooling. Then the content was taken out and the pH value thereof was again adjusted to 8.5. The obtained material was lyophilized.

The lyophilized powder thus obtained was dissolved in a 0.01 M solution of dibasic sodium phosphate and applied to an SP-Sephadex (mfd. by Pharmacia) column equilibrated with the above-mentioned buffer. Fractions eluted with 0.1 M dibasic sodium phosphate were collected and lyophilized.

The lyophilized powder was dissolved in a small amount of a 0.05 M solution of ammonium hydrogencarbonate and fractionated through a molecular sieve by using a Sephadex G-100 (mfd. by Pharmacia) column wherein the same buffer system was employed. Fractions of molecular weights of approximately 40,000 were collected and lyophilized.

The dry powder thus obtained was dissolved in a small amount of a solution of 10 mM Tris-HCl (pH 7.5) and 0.3 M sodium chloride and then fractionated by using a Concanavalin A-Sepharose (mfd. by Pharmacia) column wherein the same buffer system was employed. Fractions eluted with 0.2 M methyl mannoside were collected, sufficiently dialyzed under cooling and then lyophilized. Thus approximately 25 mg of a crude renal growth factor (RGF) was obtained.

Subsequently this crude product was fractionated and purified according to the difference in isoelectric point by using an LKB isoelectric focusing column (mfd. by LKB Produckter AB, Bromma, Sweden; capacity: 110 ml). As carrier ampholytes, Ampholine pH 3.5-10 (mfd. by LKB), Ampholine pH 9-11 (mfd. by LKB) and Ampholine pH 7-9 (mfd. by LKB) were employed. A sorbitol density gradient (5 to 50%) was prepared and the above-mentioned crude product dissolved in 2 ml of a dense solution was placed onto the center of the column (dense gradient solution: sorbitol 27 g, distilled water 34.9 ml, Ampholine (pH 9-11) 2.1 ml, and light gradient solution: sorbitol 2.7 g, distilled water 52.3 ml, Ampholine (pH 9-11) 0.3 ml, Ampholine (pH 3.5-10) 0.2 ml, Ampholine (pH 7-9) 0.2 ml). A 1 M sodium hydroxide solution and a 0.01 M acetic acid solution were used as electrode solutions. Electricity at 800 to 1500 V was turned on at 4° C. for 24 hours. After the completion of the turning of electricity, 1.5 ml portions of the material were collected with a fraction collector. Then the pH value of each fraction at 4° C. was immediately determined (COM-11: mfd. by Denki Kagaku Kogyo K. K., electrode type CE 105 C, standard buffer solution: mfd. by Wako Pure Chemicals Co., Inc.). Simultaneously the protein concentration of each fraction was determined. FIG. 1 shows the chromatographed pattern.

As a result, 104 $\mu$g, 281 $\mu$g, 415 $\mu$g and 103 $\mu$g of fractions of a pI higher than 10.32, that of 10.32 to 10.15, that of 10.15 to 9.89 and that lower than 9.89 were obtained respectively from approximately 1.5 mg of the crude renal growth factor.

Each fraction was sufficiently dialyzed under cooling to thereby remove the Ampholines and sorbitol therefrom and then lyophilized to give a powder.

The crude renal growth factor was purified several times by repeating the isoelectric focusing under the same conditions as those employed above. Then fractions of the same mean pI range were combined together. The pI of equine cardiac myoglobin (Type III: mfd. by Sigma Chemical Co.,) used as a standard protein was 7.97.

Evaluation of Renal Growth Promoting Activity

It was determined which fraction among those obtained above would promote renal growth.

The renal growth promoting effect of renotropin was determined with the guidance of the promotion of the DNA-synthesizing effect of renal cells.

Male CD rats (available from Nippon Charles River Co. and born on the same day (average body weight: 100 g)) were subjected to hypophysectomy and castration and then fed for nine days. After confirming whether the operation had been appropriately carried out or not, the rats were divided into test lots and a control lot each consisting of at least five animals.

50 $\mu$g of each fraction fractionated by the above isoelectric focusing was dissolved in 150 $\mu$l of a 50 mM borate buffer (pH 7.5) containing 0.1% of BSA and subcutaneously injected into each rat. After eight hours, the animal was sacrificed by cutting off the head and blood-drawn, and then the right and left kidneys were taken out. After peeling off the capsule, two slices of each kidney were prepared along the corticomedullary axis. These slices were incubated in 2 ml of Krebs-Ringer bicarbonate buffer (pH 7.5) at 37° C. for two hours. This buffer had been preliminarily aerated with a gas mixture comprising 95% of oxygen and 5% of carbon dioxide and then 2 $\mu$Ci/ml of 1,2-methy$^3$H-thymidine (mfd. by New England Nuclear Corp.) had been added thereto. After the completion of the incubation, the slices were rinsed with a 4 mM thymidine solution and stored at $-20°$ C..

4 ml of distilled water was added to the stored slices and the resulting mixture was homogenized with the use of an ultradisperser (mfd. by Yamato Kagaku K.K.). Then DNA contained therein was extracted according to a process proposed by A. Fleck and H.M. Munro (cf. Biochem. Biophys. Acta, 55, 571 (1962)). The extracted DNA was hydrolyzed according to a process reported by J. R. W. Wannemacher, J. W. L. Banks and W. H. Wunner (Anal. Biochem., 11, 320 (1965)) and then determined by using bovine thymus DNA (type I, mfd. by Sigma Chemical Co.) as a standard DNA according to a process proposed by K. Burton (Biochem.J. 62, 315 (1956)). Simultaneously the radioactivity of 0.5 ml of the extracted DNA was determined in a conventional manner.

The DNA synthesis promoting activity of the renal cells was determined by radioactivity/total DNA content and expressed in the percentage of each lot by defining that of the control lot as 100%. As a result, the fraction of a pI higher than 10.32 showed a DNA synthesis promoting activity of 109%, the fraction of a pI of 10.32 to 10.15 showed that of 130% (the thick arrow in FIG. 1), the fraction of a pI of 10.15 to 9.89, which showed the largest protein content, showed no DNA synthesis promoting effect (98%) and the fraction of a pI lower than 9.89 showed that of 115% (the thin arrow in FIG. 1). Namely, the fraction of a pI of 10.32 to 10.15 and that of a pI lower than 9.89 (9.89 to 9.32) contained a renal growth promoting component. In addition, the fraction of a pI higher than 10.32 also contained the renal growth promoting component, though the activity thereof was slight.

The DNA synthesis promoting effect of the crude renal growth factor of the same batch was determined at the same time. Thus 112% of the activity was observed.

Effect of Renal Growth Promoting Component on Renal Growth in Vivo

Male CD-1 mice (available from Nippon Charles River Co. and born on the same day (average body weight: 17 g)) were subjected to hypophysectomy and castration and then fed for nine days. After confirming whether the operation had been appropriately carried out or not, the mice were divided into a test lot and a control lot each consisting of ten animals. 40 μg of the fraction of a pI of 10.32 to 10.15 as obtained above by isoelectric focusing was dissolved in 150 μl of 50 mM borate buffer (pH 7.5) containing a 0.1% BSA solution. The other 40 μg portions of the fraction of a pI of 10.32 to 10.15 were treated in the same manner. The resulting solution was subcutaneously injected into each animal at a dose of 150 μl day continuously for five days. On the sixth day, the animal was sacrificed by cutting off the head and blood-drawn, and then the right and left kidneys were taken out. After peeling off the capsule, these kidneys were lyophilized. The ratio of the weight of the dry kidneys to the final body weight of the mouse was calculated and the difference in the kidney weight between the test and control lots were examined. As a result, the test lot showed an increase in the kidney weight of 110%, which suggests that the employed fraction had a renal growth promoting effect.

Separation and Rebuilding of Subunits $\alpha$ and $\beta$ in Renal Growth Promoting Component The fraction of a pI of 10.32 to 10.15 fractionated by isoelectric focusing was subjected to high performance liquid chromatography and subunits thus separated were collected. The fraction was dissolved in a small amount of a 0.1% aqueous solution of trifluoroacetic acid (TFA) and then separated with a reversed phase column (Baker Bond wide pore butyl $C_4$: mfd. by Baker Research Products) at a linear gradient (10%–50%) with the use of 2-propanol/acetonitrile (7/3) containing 0.1% of TFA as a solvent.

Thus the subunits $\alpha$ and $\beta$ were obtained each as three main peaks named $\alpha_1$, $\beta_2$ and $\alpha_3$; and $\beta_1$, $\beta_2$ and $\beta_3$ in the order of elution. When 3 mg of the sample was separated, 230 μg of $\alpha_1$, 450 μg of $\alpha_2$, 350 μg of $\alpha_3$, 410 μg of $\beta_1$, 570 μg of $\beta_2$ and 60 μg of $\beta_3$ were obtained. As a result of the analysis of amino acid composition, etc., it was found that $\alpha_3$ and $\alpha_3$ were luteinizing hormone subunits decomposed to the lowest extent.

Equimolar amounts of $\alpha_1$ and $\beta_1$; $\alpha_2$ and $\beta_2$; and $\alpha_3$ and $\beta_3$ were mixed together. Each mixture thus, obtained was maintained at 37° C. for 48 hours in a small amount of a 1% aqueous solution of ammonium carbonate to thereby attempt to associate the subunit $\alpha$ with the subunit $\beta$. Subsequently, the mixture was desalted with a TSK gel G 3000 SW column (mfd. by Toyo Soda Mfg. Co., Ltd.) and then lyophilized. The activities of these samples were compared with one another on the basis of the DNA synthesis promoting effects as described above. As a result, the combination of $\alpha_3/\beta_3$ showed the highest activity, i.e., approximately 2.5 times as high as that of the combination of $\alpha_1/\beta_1$ in the difference from the control lot.

EXAMPLE 2

100 g of an ovine pituitary powder (mfd. by Waitaki NZ Refrigerating Ltd.) was suspended in 400 ml of cold water and then 1.5 liters of a 0.15 M ammonium sulfate solution was added thereto. 10 mM of phenylmethylsulfonyl fluoride was added thereto and the resulting mixture was homogenized with Polytron under cooling. After adjusting the pH value to 4.0, the homogenized mixture was allowed to stand for a sufficient period of time under cooling and then centrifuged. The supernatant was collected and treated in the same manner as described in Example 1. Then it was treated with an SP-Sephadex column, a Sephadex G-100 column and a Concanavalin A-Sepharose column to thereby give a crude, renal growth factor.

Further 5 mg of the crude renal growth factor was fractionated with isoelectric focusing, as in Example 1. As a result, a fraction of a pI higher than 9.85, that of a pI of 9.85 to 9.60, that of a pI of 9.60 to 9.10, that of a pI of 9.10 to 8.60, that of a pI of 8.60 to 7.30 and that of a pI lower than 7.30 were obtained. Using the same bioassay as described in Example 1, it was confirmed that the fraction of a pI higher than 9.85 contained a main renal growth promoting component.

EXAMPLE 3

750 ml of an extract of human pituitary (mfd. by Kabivitrun AB) was centrifuged. The resulting precipitate was collected and suspended in 70 ml of a 0.2 M aqueous solution of dibasic potassium phosphate. The resulting suspension was heated to 60° C. for three minutes and then dialyzed for two days under cooling. The content was taken out and 0.13 M ammonium sulfate was added thereto. After adjusting the pH value to 4.0, the pH value of the mixture was adjusted again to 3.0 with a 0.5 M metaphosphoric acid solution. Then the mixture was allowed to stand under cooling and centrifuged. The supernatant was collected, sufficiently dialyzed under cooling and then lyophilized.

Then it was treated in the same ,manner as described in Example 1 with the use of an SP-Sephadex column and a Sephadex G-100 column to thereby give an extract of crude luteinizing hormone.

This crude luteinizing hormone extract was treated with a Concanavalin A-Sephadex column to thereby give a crude renal growth factor.

The obtained crude renal growth factor was fractionated by isoelectric focusing. Each fraction thus obtained was subjected to the same bioassay as described in Example 1. As a result, it was confirmed that a fraction of a pI of 9.05 to 9.90 contained a main renal growth promoting component.

What is claimed is:

1. A method for promoting renal growth, comprising administering to a patient in need thereof an effective amount of a renal growth promoter comprising, as active component, a purified isoform of luteinizing hormone having renal growth promoting activity or a purified mixture of isoforms of luteinizing hormone which mixture has renal growth promoting activity.

2. A method in accordance with claim 1 wherein said active component is purified luteinizing hormone.

3. A method in accordance with claim 1 wherein said purified isoform or mixture of isoforms is obtained by fractionation of luteinizing hormone using difference in isoelectric point.

4. A method in accordance with claim 3 wherein said purified isoform or mixture of isoforms is that portion of luteinizing hormone which, after isoelectric point fractionation, has a pI between about 10.1 and about 10.3 or which has a pI lower than about 9.9.

5. A method in accordance with claim 1 wherein said purified isoform of mixture of isoforms contains at least 30% neutral glyco-chain component in the glyco-chain component composition of the $\beta$ subunit thereof.

6. A method in accordance with claim 1 wherein said purified isoform or mixture of isoforms contains at least 18% neutral glyco-chain component in the glyco-chain component composition of the β subunit thereof.

7. A method in accordance with claim 1, wherein said purified isoform or mixture of isoforms is that in which the α subunit is an α subunit having the longest amino acid chain and the β subunit is a β subunit having the longest amino acid chain.

8. A method in accordance with claim 7, wherein said purified isoform or mixture of isoforms is obtained by separating luteinizing hormone into α and β subunits and separating each of the subunits into groups as a function of amino acid chain length, α and β subunits each having the longest amino acid chain being selected, and reassociating said selected subunits to obtain luteinizing hormone isoforms.

9. A method in accordance with the claim 1 wherein said purified isoform or mixture of isoforms has (1) α subunits which are the same as those α subunits obtained by separating luteinizing hormone into α and β subunits, subjecting said subunits to fractionation by reverse phase liquid chromatography, and selecting those α subunits in the fractions having the lastly appearing peak among α subunit-containing peaks in an elution of chromatography, and (2) β subunits which are the same as those β subunits obtained by separating luteinizing hormone into α and β subunits, subjecting said subunits to fractionation by reverse phase liquid chromatography, and selecting those β subunits in the fraction having the lastly appearing peaks among β subunit-containing peaks in an elution of chromatography, said peaks in (1) and (2) being those which are obtainable by said separating and subjecting steps being carried out by:

(a) dissolving the luteinizing hormone in an aqueous 0.1% trifluoroacetic acid solution, (b) charging the resulting solution in a reverse phase column, and (c) performing fractionation by means of a linear gradient system comprising 0.1% trifluoroacetic acid-containing organic solvent (acetonitrile:2-propanol=3:7): aqueous 0.1% trifluoroacetic acid solution at a ratio of 10 to 50:90 to 50.

10. A method in accordance with claim 9 in which said purified isoforms or mixture of isoforms is the same as that obtained by the following process:

(1) separating a purified mixture of luteinizing hormone isoforms into α and β subunits;

(2) fractionating by reverse phase liquid chromatography the resulting α subunits and β subunits by means of said subjecting step to obtain an α subunit fraction having a lastly appearing peak among the α subunit-containing peaks and a β subunit fraction having a lastly appearing peak among β subunit-containing peaks; and (3) reassociating said obtained α and β subunit fractions to obtain luteinizing hormone isoforms.

11. A purified isoform, having α and β subunits, of luteinizing hormone, said isoform having renal growth promoting activity, or a purified mixture of isoforms, each having α and β subunits, of luteinizing hormone, said mixture having renal growth promoting activity, wherein said isoform on mixture of isoforms is that in which the α subunit is selected from the group of α subunits having the longest amino acid chain and the β subunit is selected from the group of β subunits having the longest amino acid chain.

* * * * *